United States Patent [19]

Imhof

[11] Patent Number: 4,894,064
[45] Date of Patent: Jan. 16, 1990

[54] ENDOPROSTHESIS FOR A HIP-JOINT SOCKET

[75] Inventor: Martin Imhof, Rotkreuz, Switzerland

[73] Assignee: W. Hermann AG, Steinhausen, Switzerland

[21] Appl. No.: 267,314

[22] Filed: Nov. 4, 1988

[30] Foreign Application Priority Data

Nov. 9, 1987 [CH] Switzerland ................. 4364/87

[51] Int. Cl.$^4$ .............................................. A61F 2/36
[52] U.S. Cl. ....................................................... 623/22
[58] Field of Search ..................... 623/16, 18, 22, 23

[56] References Cited

U.S. PATENT DOCUMENTS

| 4,450,592 | 5/1984 | Niederer et al. | 623/22 |
| 4,662,891 | 5/1987 | Noiles | 623/22 |
| 4,715,859 | 12/1987 | Schelhas et al. | 623/22 |

FOREIGN PATENT DOCUMENTS

| 524051 | 5/1931 | Fed. Rep. of Germany. |
| 2950536 | 7/1981 | Fed. Rep. of Germany. |
| 3446048 | 10/1985 | Fed. Rep. of Germany. |
| 8500867 | 1/1986 | Fed. Rep. of Germany. |
| 2572277 | 5/1986 | France | 623/22 |
| 2597329 | 11/1987 | France | 623/22 |

Primary Examiner—Richard J. Apley
Assistant Examiner—David J. Isabella
Attorney, Agent, or Firm—Wenderoth, Lind & Ponack

[57] ABSTRACT

A shell sleeve serves for the reception of a bearing socket. The shell sleeve possesses the shape of a body of revolution or rotation which tapers or narrows towards a pole region. This body of revolution carries at its outer surface a self-tapping thread. To facilitate threading-in of the shell sleeve into the bone substance or material and to preclude, during such threading-in operation, the application of forces which would cause any pressure and splintering action upon the bone substance or material, the thread comprises a flat thread. This flat thread has flanks dispositioned at essentially right angles to the lengthwise axis of the body of revolution and the spacing from thread flight to thread flight is constant. The portions of the thread flights which follow a related cutter or cutting surface thereof are undercut or machined back.

7 Claims, 1 Drawing Sheet

ENDOPROSTHESIS FOR A HIP-JOINT SOCKET

BACKGROUND OF THE INVENTION

The present invention relates to a new and improved construction of an endoprosthesis for a hip-joint socket which is of the type comprising a shell or jacket sleeve intended to receive a bearing or support socket. The shell or jacket sleeve possesses the shape of a body of revolution or rotation which tapers or narrows towards a pole or apex region and which carries a self-tapping or self-cutting thread or threading at its outer surface.

In this respect, it is to be noted that also in the context of the present development the expression "self-tapping thread" or "self-cutting thread" designates a thread or threading wherein the thread flight or course for each revolution or convolution is subdivided into sections or portions by a plurality of gaps or openings, and the trailing wall of each gap, as viewed in the threading-in direction, forms a cutting surface or cutter, the cutter shape of which is governed by the thread profile or sectional shape.

Endoprostheses of the previously mentioned type are known in this technology. The shape of the shell or jacket sleeve results in the fact that also the self-tapping thread can be compared to a certain extent to a conical external thread. With the state-of-the-art endoprostheses, the self-tapping thread possesses the profile or sectional shape of approximately a pointed thread or a trapezoidal thread, and the thread pitch is approximately constant at all thread sections or portions.

Since, as stated, the thread or threading can be compared to a conical thread and with the heretofore constructions of endoprostheses the thread pitch is constant at all thread sections, during threading-in of the shell sleeve into the substance of the bone, the sections of the thread which follow the cutters exert a pressure upon the bone substance both in radial direction and in axial direction in a manner such as if at the neck or entrance opening of the so-to-speak female thread which has been cut into the bone substance, there were driven-in wedges in the circumferential direction. As a result, for the threading-in of the shell sleeve, there must be applied a comparatively high torque or rotational moment. Hence, the operating surgeon does not always sense the point in time when the shell sleeve has been threaded-in to a satisfactory depth. Moreover, with the heretofore known constructions of the prior art endoprostheses, there cannot be totally eliminated the risk that a fissure or crack will form in the bone substance or material due to the aforementioned prevailing pressure. Furthermore, this bone fissure need not necessarily occur during the implantation, rather, and this is even worse, when following the surgical operation the implanted hip-joint is again subjected to normal loads. An incompletely threaded-in sleeve and/or the formation of fissures in the bone substance result in a loose seating of the implanted hip-joint socket and possibly can result in the detrimental consequence that there is required a renewed surgical operation.

SUMMARY OF THE INVENTION

Therefore with the foregoing in mind it is a primary object of the present invention to provide a new and improved construction of an endoprosthesis for a hip-joint socket which does not suffer from the aforementioned drawbacks and shortcomings of the prior art constructions.

Another and more specific object of the present invention, aims at the provision of a new and improved construction of an endoprosthesis of the previously mentioned type which can be threaded comparatively easily into a cavity or recess which has been prepared in the bone substance or material and during the threading-in operation there is not exerted any pressure or any appreciable pressure upon the substance or material of the bone.

Now in order to implement these and still further objects of the invention, which will become more readily apparent as the description proceeds, the endoprosthesis for the hip-joint socket of the present development, among other things, is manifested by the features that the thread or threading comprises a flat thread or threading. The flanks of such thread or threading are disposed approximately at right angles or orthogonally with respect to the lengthwise axis of the body of revolution or rotation. The spacing from thread flight or course to thread flight or course of the thread or threading is essentially constant and the thread sections or portions of the thread flights or courses which follow the cutters or cutting surfaces are undercut or machined back.

By virtue of the fact that the thread or threading comprises a flat thread or threading the sections or portions of the thread flanks which follow the cutting surfaces or cutters do not exert any axial pressure upon the flanks of the "female thread" which has been cut into the substance or material of the bone. By the same token, the sections or portions of the threads which follow the cutting surfaces or cutters since by virtue of the provision of the undercut or machining back thereof, do not exert any radial pressure upon the base of the female thread which has been cut into the bone substance or material.

BRIEF DESCRIPTION OF THE DRAWINGS

The invention will be better understood and objects other than those set forth above will become apparent when consideration is given to the following detailed description thereof. Such description makes reference to the annexed drawings wherein throughout the various figures of the drawings, there have been generally used the same reference characters to denote the same or analogous components and wherein.

DETAILED DESCRIPTION OF THE PREFERRED EMBODIMENTS

Figure 2:
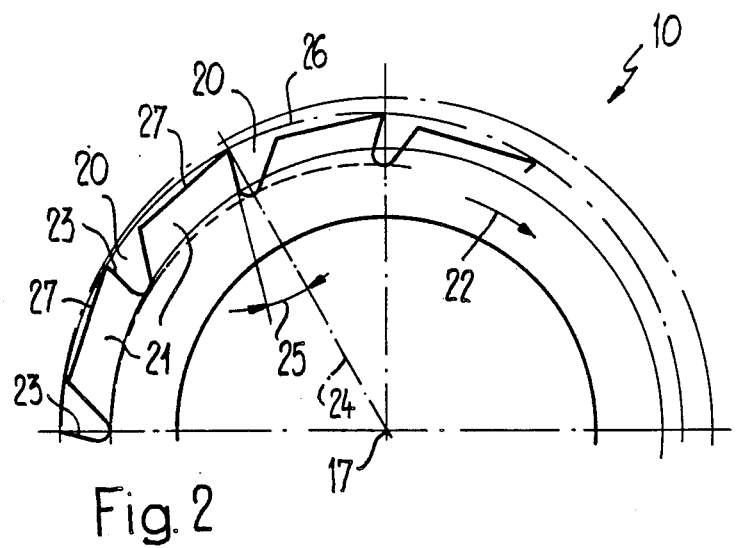
FIG. 2 is a front view of the shell or jacket sleeve of the endoprosthesis depicted in FIG. 1 looking substantially in the direction of the arrow II thereof.

Describing now the drawings, it is to be understood that to simplify the showing thereof, only enough of the construction of the exemplary embodiment of endoprosthesis for a hip-joint socket has been illustrated therein as is needed to enable one skilled in the art to readily understand the underlying principles and concepts of this invention. Thus in the drawings of FIGS. 1 and 2 there has been only depicted the shell or jacket sleeve or sleeve member 10 of the endoprosthesis. This shell or jacket sleeve 10 essentially possesses the shape of a body of revolution or rotation which tapers or narrows towards its pole or apex region 13. Furthermore, the shell or jacket sleeve 10 possesses a here only schematically illustrated cavity or recess 11 which is intended to receive a not particularly illustrated bearing or support socket formed of a suitable synthetic or plastics material, for instance formed of polyethylene. Also to facilitate the drawing illustration there likewise has not been shown the notches or grooves which may be possibly provided in the cavity or recess 11 for anchoring the bearing or support socket and the, for instance, bores or the like which are provided at the base surface or region 12 of the shell or jacket sleeve 10 in order to apply a suitable threading-in tool for accomplishing the threading-in of the shell or jacket sleeve 10.

In the embodiment under discussion the outer shape or configuration of the shell or jacket sleeve 10 is comparable to that of a so-to-speak "stepped cone", hose apex or pole region or area 13 of which is formed by a segment of a sphere. The stepped cone carries at its outer surface or side a self-tapping or self-cutting thread or threading 14. As will be observed by referring to the left-hand portion of FIG. 1, the thread 14 possesses the profile or sectional shape of a flat thread or threading, and the generatrix of the thread flanks 15 and 16 is located essentially at right angles or orthogonally with respect to the lengthwise axis 17 of the shell or jacket sleeve or sleeve member 10. The pitch or spacing 18 from thread flight or course 14a to thread flight or course 14a is essentially constant and amounts to a multiple of the thickness 19 of each thread flight or course 14a. Equally, the thickness 19 of each thread flight or course 14a is essentially constant. The depth of each thread flank 15 and 16 of the thread 14 may be more than twice the thickness 19 of each thread flight 14a. It is also here remarked that the helix angle of the tapering helical surfaces of the thread flanks 15 and 16 is constant as measured at the point of intersection of each thread flight 14a with a virtual or imaginary straight line, illustrated in FIG. 1 as a chain-dot or phantom line and designated by reference character G, which extends substantially parallel to the lengthwise axis 17 of the shell sleeve 10.

Figure 1:
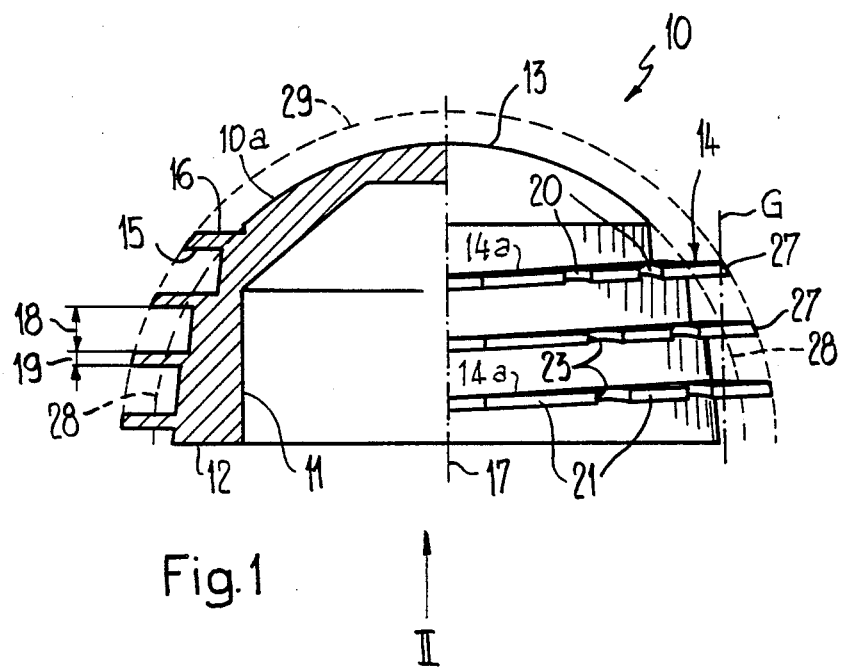
FIG. 1 illustrates in side view and partially axial sectional view a shell or jacket sleeve of an endoprosthesis, there being shown at the right-hand side of the illustration the mentioned side view and at the left-hand side the mentioned axial sectional view.

Just as is the case for every self-tapping thread, and as will be observed by referring to the right-hand portion of FIG. 1 and the left-hand portion of FIG. 2, each thread flight 14a is subdivided into thread sections or portions 21 by the provision of gaps or openings 20. The side surface of each of these gaps 20, constituting a trailing side surface as viewed in the thread-in direction, indicated generally by the arrow 22 in FIG. 2, of the shell or jacket socket 10, thus forms a cutting surface or cutter 23. Each such cutting surface or cutter 23 possesses a "rake angle" or cutting angle 25, for instance in the order of magnitude between 15° and 30°, in relation to a radial plane 24 taken through the aforementioned lengthwise axis 17.

Since the thread or threading 14 protrudes radially from a tapering base body 10a, the envelope line of the apex of the thread flights 14a of the thread or threading 14 does not constitute a circle, rather a spiral when projected in the direction of the lengthwise axis 17. This spiral has been indicated by the phantom or chain-dot line 26 in FIG. 2. Furthermore, and as will be observed by further inspecting FIG. 2 the apex surfaces 27 of all of the thread sections or portions 21 of the thread 14 and which follow a related one of the cutting surfaces or cutters 23 are undercut with respect to this spiral 26. These apex surfaces 27 also can be machined back or so-to-speak backed-off with respect to the spiral 26, for instance by using a lathe. Hence, the term "undercut" as employed herein and in the claims is tended to encompass both working or machining possibilities.

From what has been discussed previously, it will be understood that independent of how deeply the shell sleeve or sleeve member 10 has already been threaded-in, in all instances it is only the apex region of the momentarily effective cutting surface or cutter 23 which actually digs or claws into the bone substance or material of the appropriately prepared cavity or recess in the bone. Since there is provided a flat thread the thread flanks 15 and 16 do not exert any axial pressure upon the bone substance or material and, furthermore, since the apex surfaces 27 are, as explained, "undercut", these apex surfaces 27 do not exert any radial pressure. The bone substance or material which is cut out during cutting of the so-to-speak "female thread" in the bone is accommodated in the gaps 20 and again solidifies or hardens after a comparatively brief amount of time.

Having now had the benefit of the previously described construction of endoprosthesis for a hip-joint socket, there will be considered the steps or operating procedures which are performed for the implantation of the described shell or jacket sleeve 10 and which are as follows:

By means of a suitable tool, such as one which is comparable to a rose bit there is formed or worked in the bone substance or material a cavity or recess in the form of a segment of a sphere. The profile or sectional shape of this sphere segment has been indicated in FIG. 1 by the phantom or chain-dot line 28 and possesses the same radius as the spherical segment of the apex or pole region 13 of the shell or jacket sleeve 10. Now the shell or jacket sleeve 10 can be threaded-in until the apex or pole region 13 snugly bears against the apex region of the cavity or recess which has been formed in the bone substance or material. During such operation, there is not exerted any wedging or pressure or compression action upon the bone substance or material. The insertion of the bearing or support socket, to the extent that it has not yet been inserted, is then accomplished in conventional manner.

As far as the fabrication of the heretofore described shell or jacket sleeve 10 is concerned the following is noted:

In the exemplary embodiment under discussion there is started with a blank or workpiece, for instance formed of a titanium alloy and in the shape of a semisphere, as such has been indicated by the broken line 29 in FIG. 1. Then there is formed the cavity or recess 11. Now there can be machined the spherical segment 13 and/or there can be cut the threads or threading 14. For forming the threads or threading 14 there is employed a profile steel of the cutting width 18 which is advanced during each revolution by the distance constituting the sum of the dimensions 18 and 19 designating respectively, the thread pitch or spacing and thickness of each thread flight or course 14a, whereas the advancement in the direction of the lengthwise axis 17 is accomplished in a number of stages or steps and in a number of throughpasses until there has been , obtained the desired thread depth. Finally, there are :1 machined, as by milling by using for instance a profile miller, the gaps or openings 20 which, for instance, extend along a meridian. By means of a further miller or milling tool, there are finally undercut the apex surfaces 27 in relation to the outermost section or portion of the related cutting surface or cutter 23.

The described shell or jacket sleeve or sleeve member 10 affords a snug seat or tight fit in the bone substance or material, since the thread flanks 15 and 16 bear snugly, however so-to-speak without exerting any pressure or compression, over the entire length of the associated thread section or portion 21.

Although in the described exemplary embodiment, the base body 10a of the shell or jacket sleeve 10 possesses the shape or form of a stepped cone which is terminated by a spherical segment, the described flat thread or threading can be perfected at base bodies having an optional generatrix, for instance at a generatrix of an arc (semi-sphere), two straight lines (truncated cone). Also the apex or pole region or area 13 can possess a roughened surface structure or roughening which during the regeneration of the bone substance or material promotes bone growth thereat. Finally, also a through-hole or continuous opening can be provided at the apex region of the shell or jacket sleeve.

While there are shown and described present preferred embodiments of the invention, it is to be distinctly understood that the invention is not limited thereto, but may be otherwise variously embodied and practiced within the scope of the following claims.
ACCORDINGLY,

What I claim is:

1. An endoprosthesis for a hip-joint socket, comprising:
    a shell sleeve member capable of receiving a bearing socket;
    said shell sleeve member possessing a pole region and an outer surface;
    said shell sleeve member possessing the shape of a body of revolution which tapers towards said pole region;
    self-tapping thread means provided at said outer surface of said shell sleeve member;
    said self-tapping thread means comprising substantially flat upper and lower thread flanks;
    said body of revolution defining a lengthwise axis;
    said upper and lower thread flanks being parallel and disposed at approximately right angles to said lengthwise axis of said body of revolution;
    said self-tapping thread means comprising thread flights which are spaced from one another;
    said self-tapping thread means having an essentially constant pitch;
    each of said thread flights having cutting means formed therein;
    said cutting means being circumferentially spaced from each other along each said thread flight and defining thread portions between each two successive cutting means; and
    each one of said thread portions defining a circumferential portion containing an undercut region.

2. The endoprosthesis as defined in claim 1, wherein:
    each of said thread flights has a thread thickness;
    said substantially flat thread flanks of said self-tapping thread means protruding from said outer surface of said shell sleeve member by a predetermined flank depth as viewed in a direction away from said lengthwise axis of said body of revolution of said shell sleeve member; and
    said flank depth of said self-tapping thread means being more than twice said thread thickness of a thread flight.

3. The endoprosthesis as defined in claim 2, wherein:
    the spacing from thread flight to thread flight of the self-tapping thread means is greater than said thread thickness of a thread flight.

4. The endoprosthesis as defined in claim 1, wherein:
    each of said thread flights has a predetermined thickness; and
    the spacing from thread flight to thread flight of said self-tapping thread means is greater than said predetermined thickness of each of the thread flights.

5. The endoprosthesis as defined in claim 1, wherein:
    said self-tapping thread means provided at said outer surface of said shell sleeve member assume a helical configuration defining a predetermined helix angle; and
    the helix angle of all of said thread flights of said self-tapping thread means being essentially of the same magnitude.

6. The endoprosthesis as defined in claim 1, wherein:
    each of said cutting means defines a cutting surface;
    each of said cutting surfaces possessing a cutting angle formed between the cutting surface and an associated plane extending substantially in radial direction of said body of revolution of said shell sleeve member; and
    said cutting angle having a value in a range of 10° to 30° as viewed in a direction opposite to a predetermined threading-in direction of the endoprosthesis.

7. The endoprosthesis as defined in claim 1, wherein:
    each of said cutting means defines a cutting surfaces;
    each cutting surface having an outermost portion formed at an intersection with an associated thread portion; and
    said outermost portions of the cutting surfaces defining an envelope surface which is substantially coaxial with respect to the lengthwise axis of said body of revolution of said shell sleeve member.

* * * * *